United States Patent
Cleland et al.

(10) Patent No.: US 11,420,058 B2
(45) Date of Patent: Aug. 23, 2022

(54) NERVE ROOT AND DORSAL ROOT GANGLION STIMULATION FROM THE LATERAL EPIDURAL SPACE

(71) Applicant: Medtronic, Inc., Minneapolis, MN (US)

(72) Inventors: Andrew Jay Cleland, St. Paul, MN (US); Melanie D. Goodman Keiser, Otsego, MN (US); Louis Vera-Portocarrero, St. Anthony, MN (US); Phillip C. Falkner, Minneapolis, MN (US); Brooke Kelley, Brooklyn Center, MN (US); Jiashu Li, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/086,070

(22) Filed: Oct. 30, 2020

(65) Prior Publication Data

US 2022/0134109 A1    May 5, 2022

(51) Int. Cl.
*A61N 1/36*    (2006.01)
*A61N 1/05*    (2006.01)

(52) U.S. Cl.
CPC ....... *A61N 1/36071* (2013.01); *A61N 1/0551* (2013.01); *A61N 1/36062* (2017.08); *A61N 1/36182* (2013.01)

(58) Field of Classification Search
CPC .............. A61N 1/0551; A61N 1/36062; A61N 1/36182; A61N 1/36071
See application file for complete search history.

(56) References Cited

U.S. PATENT DOCUMENTS

| | | | |
|---|---|---|---|
| 7,047,084 B2 | 5/2006 | Erickson et al. | |
| 8,135,476 B2 * | 3/2012 | Gerber | A61N 1/36007 607/116 |
| 8,744,597 B2 | 6/2014 | King et al. | |
| 9,259,568 B2 | 2/2016 | Zhao et al. | |
| 9,259,569 B2 | 2/2016 | Brounstein et al. | |
| 9,656,085 B2 | 5/2017 | Moffitt et al. | |

(Continued)

FOREIGN PATENT DOCUMENTS

WO    2009/134350    11/2009

OTHER PUBLICATIONS

Extended European Search Report for European Application No. 21204765.8, dated Mar. 22, 2022; 8 pages.

*Primary Examiner* — Alyssa M Alter
(74) *Attorney, Agent, or Firm* — Mueting Raasch Group (57) ABSTRACT

A system comprises a bendable, pre-formed lead body operable to be implanted proximate a neural pathway of a patient. A first electrode comprising a plurality of first segments at a first longitudinal location of the lead body is configured to be positioned at a lateral epidural region proximate at least one nerve root of the patient, and a second electrode comprising a plurality of second segments at a second longitudinal location of the lead body is configured to be positioned along a midline of the patient's spinal column. The system further includes a signal generator electrically coupled to at least one of the first and second electrodes and a processor coupled to the signal generator and operable to apply a stimulation signal to at least one of the first and second electrodes.

16 Claims, 5 Drawing Sheets

(56) References Cited

U.S. PATENT DOCUMENTS

| | | |
|---|---|---|
| 9,737,715 B2 | 8/2017 | Moffitt et al. |
| 9,764,141 B2 | 9/2017 | Moffitt et al. |
| 9,814,880 B2 | 11/2017 | Hershey et al. |
| 2007/0150034 A1 | 6/2007 | Rooney et al. |
| 2010/0004721 A1 | 1/2010 | Fattouh et al. |
| 2010/0292769 A1* | 11/2010 | Braunstein ......... A61N 1/36071 607/117 |
| 2011/0276056 A1 | 11/2011 | Grigsby et al. |
| 2015/0005860 A1 | 1/2015 | Howard et al. |
| 2017/0333702 A1 | 11/2017 | Barner |
| 2020/0009374 A1 | 1/2020 | Howard et al. |

* cited by examiner

NERVE ROOT AND DORSAL ROOT GANGLION STIMULATION FROM THE LATERAL EPIDURAL SPACE

FIELD

The present technology is generally related to medical devices and, more specifically, systems, devices, and methods for stimulating spinal nerve roots and dorsal root ganglion from the lateral epidural space.

BACKGROUND

Spinal cord and dorsal root ganglion stimulation are used to alleviate pain. Spinal cord stimulation may be selected to provide relief to a general area as stimulation over the spinal cord captures axons from multiple dermatomes. Dorsal root ganglion stimulation may be selected instead as a lower amplitude may be used for stimulation due to minimal cerebrospinal fluid over the ganglion, fixed lead placement may be effected with a natural anchoring in the foramen, and targeted stimulation distribution is possible as the dorsal root ganglion is comprised of axons from a specific dermatome. However, dorsal root ganglion stimulation is a more difficult procedure requiring advanced training, placing a lead through the foramen can be painful, multiple leads may be required to cover a pain relief area, there is a high complication rate from lead fracture, and foraminal stenosis can be exacerbated. The benefits of dorsal root ganglion stimulation can be achieved while minimizing these disadvantages and side effects as described herein.

SUMMARY

In an embodiment, a system comprises a bendable, preformed lead body operable to be implanted proximate a neural pathway of a patient. A first electrode comprises a plurality of first segments at a first longitudinal location of the lead body and is configured to be positioned at a lateral epidural region proximate at least one nerve root of the patient, and a second electrode comprises a plurality of second segments at a second longitudinal location of the lead body and is configured to be positioned along a midline of the patient's spinal column. A signal generator is electrically coupled to at least one of the first and second electrodes, and a processor is coupled to the signal generator and operable to apply a stimulation signal to at least one of the first and second electrodes.

In another embodiment, a system comprises a lead body operable to be implanted proximate a target nerve root area of a patient. A first electrode is positioned at a first longitudinal location of the lead body, and a second electrode is positioned at a second longitudinal location of the lead body forming a pair of electrodes with the first electrode. The second electrode is spaced apart from the first electrode at a distance, D, determined by at least one of the size of the target nerve root area and distance between the electrode pair and the target nerve root area. A signal generator is electrically coupled to at least one of the first and second electrodes, and a processor is coupled to the signal generator and operable to apply a stimulation signal to at least one of the first and second electrodes.

A further embodiment is directed to a system comprising a lead body operable to be implanted proximate a plurality of nerve roots of a patient having a first set of electrodes at a first longitudinal location of the lead body and a second set of electrodes at a second longitudinal location of the lead body. The second set of electrodes is spaced apart from the first set of electrodes by a first distance determined by a spacing between a first nerve root and a second nerve root of the patient. A third set of electrodes is positioned at a third longitudinal location of the lead body, and the third set of electrodes is spaced apart from the second set of electrodes by a second distance, wherein the second distance is different from the first distance and determined by a spacing between the second nerve root and a third nerve root of the patient. A signal generator is electrically coupled to at least one of the first and second electrodes, and a processor is coupled to the signal generator and operable to apply a stimulation signal to at least one of the first and second electrodes.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The discussion below refers to the following figures, wherein the same reference number may be used to identify the similar/same component in multiple figures. However, the use of a number to refer to a component in a given figure is not intended to limit the component in another figure labeled with the same number. The figures are not necessarily to scale.

DETAILED DESCRIPTION

The present disclosure is generally related to electrical stimulation therapy. For example, medical devices may be used to deliver electrical stimulation therapy to a patient proximate specific locations along the spinal column to treat chronic pain. Providing electrical stimulation proximate a dorsal root ganglion or nerve root can specifically target a dermatome so as to avoid unnecessarily stimulating unaffected tissues. However, placing a lead for dorsal root ganglion stimulation involves placing the lead through the foramen, which can be painful for a patient, and multiple leads may be required (i.e., a new lead at every vertebral level and each side) to cover the area of pain, which together generate a high complication rate from lead fracture.

Minimizing the number of electrodes (and leads) implanted in the body can reduce the sizes of the implanted device components and be more comfortable for a patient (e.g., fewer wires, thinner leads). So long as the smaller components are robust enough to resist fracture, they can also improve patient safety. Stimulating a nerve root or dorsal root ganglion by placing a lead laterally in the epidural space provides benefits of nerve root and dorsal root ganglion stimulation while minimizing or avoiding the side effects of placement in the foramen. To target specific, desired nerve roots and/or dorsal root ganglions, controlling the electrode spacing within a lead provides increased accuracy of electrode placement. This customized spacing may be coupled with directional electrodes and/or pre-shaped leads to improve targeted stimulation with fewer leads and/or electrodes thereby improving patient safety and comfort.

Figure 1A:
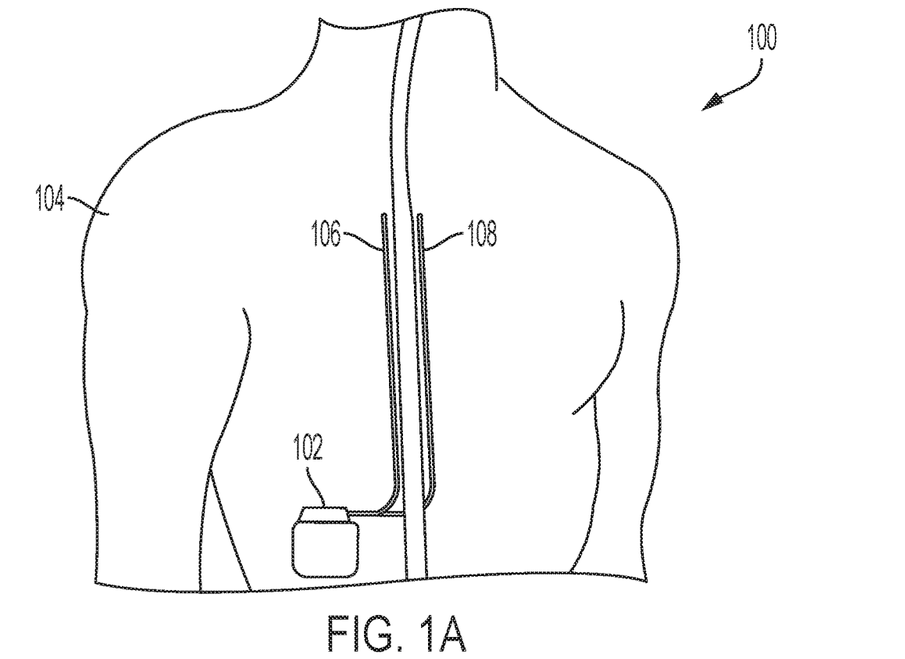
FIG. 1A is a simplified diagram of an implantable system according to an example embodiment.

In FIG. 1A, a diagram illustrates a system 100 according to an example embodiment. The system includes an implantable therapy device 102 configured to deliver electrical stimulation therapy to patient 104. In the illustrated example, the therapy device 102 is configured to deliver spinal cord stimulation therapy using devices and methods described herein. Although the methods and apparatuses described in this disclosure are generally applicable to a variety of medical devices including external and implantable medical devices, embodiments of implantable electrical stimulators (e.g., neurostimulators) will be described for purposes of illustration. For example, an implantable spinal cord stimulation system 100 is shown for purposes of illustration, but without limitation as to other types of medical devices or other therapeutic applications of medical devices.

As shown in FIG. 1A, the implantable device 102 is electrically coupled to one or more leads 106, 108. The implantable device 102 is configured as an electrical stimulator that generates and delivers electrical stimulation therapy to patient 104 via electrodes of leads 106, 108, e.g., for relief of chronic pain or other symptoms. The implantable device 102 may use more or fewer leads 106, 108.

In addition to electrical stimulation therapy, the implantable device 102 may also be configured to generate and deliver control pulses configured to elicit evoked compound action potential (ECAP) signals that may or may not contribute to the therapy of informed pulses. As discussed herein, the control pulses may be non-therapeutic. The implantable device 102 may be a chronic electrical stimulator that remains implanted within patient 104 on the order of days to years. The implantable device 102 may be a temporary, or trial, stimulator used to screen or evaluate the efficacy of electrical stimulation for chronic therapy. In one example, implantable device 102 is implanted within patient 104, while in another example, implantable device 102 is an external device coupled to percutaneously implanted leads 106, 108.

Figure 1B:
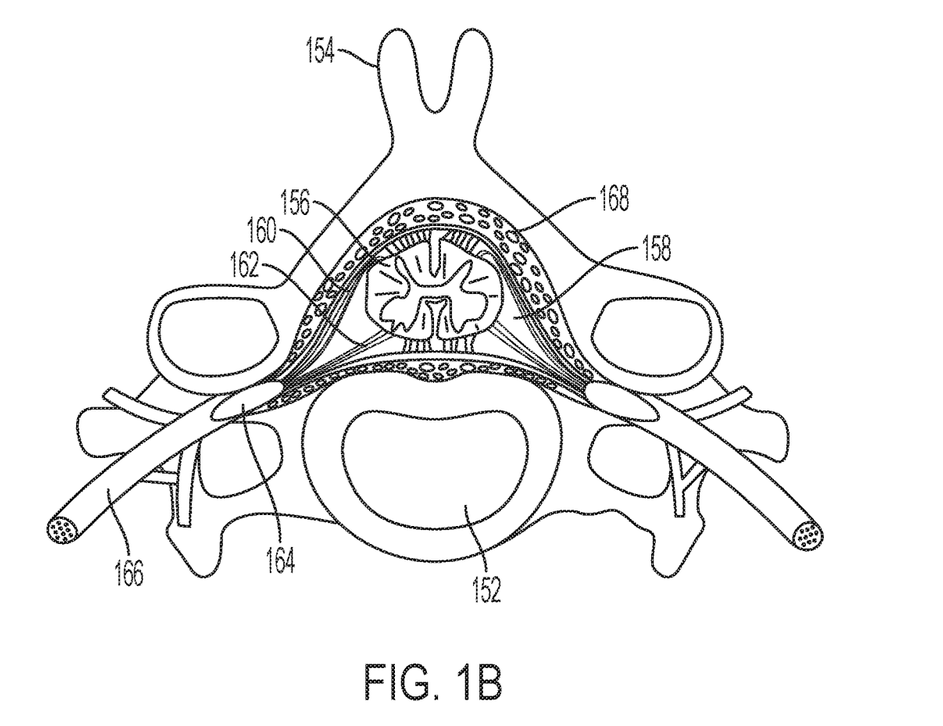
FIG. 1B is a top-down view simplified diagram of the anatomy of a vertebra of a human spinal column.

The leads 106, 108 may be positioned laterally in the epidural space of the patient's 104 spinal column. FIG. 1B provides a simplified top-down diagram of a single vertebra. The vertebra includes a vertebral body 152 and a bony ring that includes the spinous process 154. The spinal column 156 is surrounded by cerebrospinal fluid 158 and is positioned between the vertebral body 152 and bony ring. A dorsal root 160 and ventral root 162 extend from the spinal column 156 toward the vertebral body 152 on both the right and left sides. The dorsal root ganglion (DRG) 164 is positioned at the distal end of the dorsal root 160 and contains the neuron cell bodies of the nerve fibers conveyed by the root. The dorsal root 162 and the ventral root 162 join to form a mixed spinal nerve 166. The space between the bony ring and the spinal column 156/dorsal root 160 is called the epidural space 168. To target specific one or more nerve roots and/or one or more DRGs, one or more leads 106, 108 are positioned in the epidural space.

The leads 106, 108 can be a percutaneous stimulation lead used to deliver various stimulation therapies. In some implementations, a percutaneous stimulation lead has cylindrical electrodes arrayed longitudinally along a lead body. Electrical stimulation therapy may be delivered by applying a series of electrical stimulation pulses to a selected set of the electrodes. In some types of therapy, some of the electrodes on the lead can be configured to sense an ECAP to the stimulation pulses. The stimulation pulses may be therapeutic or non-therapeutic, and the sensed ECAP response facilitates measuring the efficacy of the applied pulses. The ECAP measurements can be used to adjust the therapy (e.g., pulse width, amplitude, frequency, overshoot) to improve the efficacy of the treatment. The measurement of the ECAP response allows for, among other things, the manual or automatic adjustment of the implantable device to compensate for changing conditions over the life of the device. Examples of changing conditions include shifting of position/orientation of the lead within the body, changing physiology of the patient, etc.

In some implementations, the percutaneous stimulation lead body is an elongated cylindrical tube, which can be implanted using relatively non-intrusive surgical procedures. The electrodes on such a lead may be cylindrical rings arrayed longitudinally down the length of the lead. To provide the therapy, two or more electrodes may be configured to provide stimulation therapy, e.g., being electrically coupled to respective positive and negative outputs of a pulse generator. For an ECAP process, two or more different electrode (e.g., at a distal end of the lead) segments may be electrically coupled to sense the evoked response, with one electrode being coupled as an anode and the other as a cathode. The lead may have any number of electrodes (e.g., more than four) to allow for customizing the location of the stimulation and sensing. This customization can be performed electronically by the selection of different subsets of the electrodes for each function, e.g., using a switching circuit.

Percutaneous, epidural, cylindrical electrodes for spinal cord stimulation may provide poor targeting of the stimulation field to the target neural structures. For therapies such as spinal cord stimulation, and specifically, DRG and nerve root stimulation, the lead may be positioned in an epidural space near the dorsal column of the patient's spine. In this location, one side of the lead is facing the nerve tissue of the spinal cord. The part of the stimulation electrodes facing away from the spinal cord are emitting into tissue that is not being treated, and the part of the sensing electrodes facing away from the spinal cord are picking up electromagnetic impulses that may not be related to the treatment.

In some embodiments described herein, directional subcutaneous lead electrodes are configured to sense and emit electromagnetic fields over a first partial circumference of the lead body, such that there is no respective sensing and emission along second partial circumference at the same longitudinal location. The second partial circumference is different than the first partial circumference, e.g., the partial circumferences may be non-overlapping. This may be achieved by segmenting the electrodes at each longitudinal location, and/or by covering parts of fully circumferential electrodes (e.g., ring electrodes) with an electrical insulator that suppresses emission/sensing along the covered portions. The segmented electrodes may be controlled to steer the resulting fields to capture a nerve root or DRG (e.g., cathode towards the target structure and anode away). Further steering may be achieved by staggering directional electrodes with nondirectional electrodes to save contacts and extend the lead to cover more nerve roots. Similar to any of the lead electrodes, the segments of the directional electrodes are individually programmable using different parameters, such as, ping, synchronous, asynchronous, continuous, discontinuous, etc.) to control the depth of field for the stimulation. Another technique for targeting specific nerve root or DRG structures is to modify the shape of the lead.

Figure 2A:
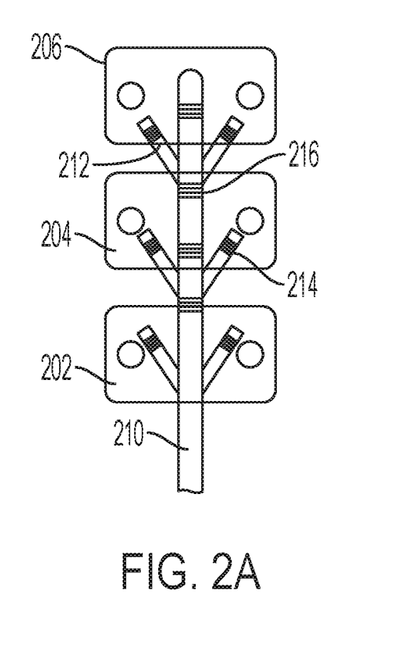
FIG. 2A is an illustration of an implanted lead with bi-directional branches according to an example embodiment.

FIGS. 2A-2D illustrate examples of branched lead configurations for positioning in the epidural space to stimulate one or more nerve roots and DRGs. In FIG. 2A, a main lead body 210 extends among three vertebra 202, 204, 206 and three sets of nerve roots and DRGs. The lead body 210 includes branches that extends to the left 212 and branches that extend to the right such that the lead may be considered to have bi-directional branches. The branches may also extend in the dorsal and ventral directions as well. As set forth above, the lead includes a plurality of electrodes 216 in the lead body as well as one or more electrodes 214 in the respective branches. Each of the electrodes 214, 216 may be configured as discussed above.

Figure 2B:
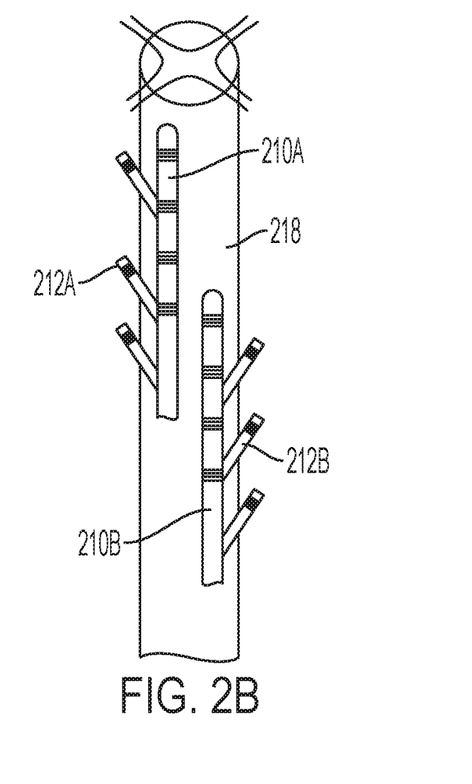
FIG. 2B is an illustration of a pair of implanted leads each having uni-directional branches according to an example embodiment.

FIG. 2B illustrates an example embodiment of a unidirectional branched lead. The lead again includes a main lead body 210A; however, the branches 212A extend in one direction away from the lead body 210A (e.g., to the left). As shown, multiple uni-directional branched leads may be used in combination. For example, lead body 210A and respective branches 212A is positioned proximate the spinal column 218 at a first position (e.g., proximate targeted vertebrae), and a second lead body 210B with respective branches 212B that extend in a direction opposite that of branches 212A (e.g., to the right) is positioned proximate the spinal column 218 at a second position. The second position may be proximate different targeted vertebrae that in certain embodiments are adjacent those of the first position. The branched lead configurations can perform capture with a single lead for DRG stimulation. Utilizing a combination of two or more branched leads increases the field generation options for targeting multiple nerve root and/or DRG sites to cover a more complicated or larger pain area. The increased options provided by the branched lead configurations also allows for multiple stimulation fields using fewer leads.

Figure 2C:
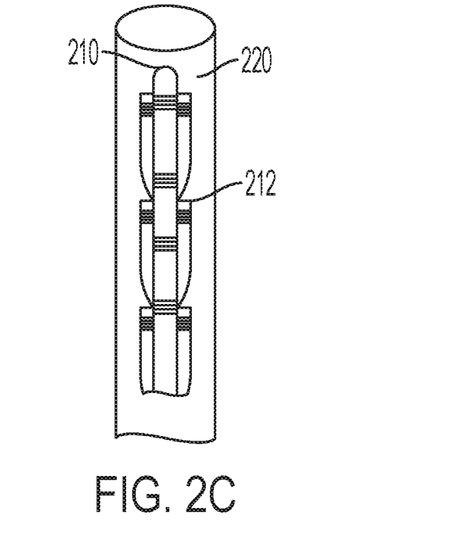
FIG. 2C is an illustration of the lead of FIG. 2A within a catheter sheath according to an example embodiment.
Figure 2D:
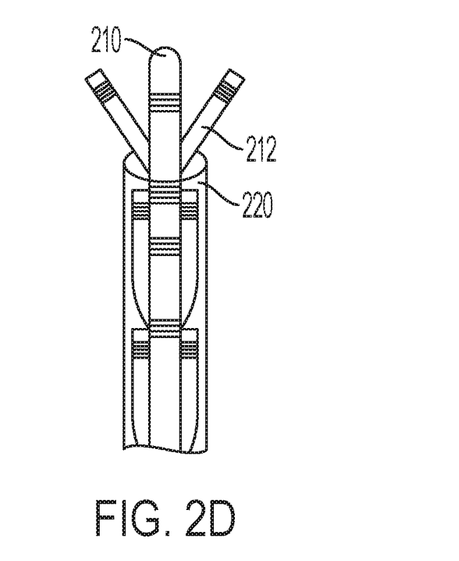
FIG. 2D is an illustration of the lead of FIG. 2D as the catheter sheath is removed according to an example embodiment.

The branched leads of FIGS. 2A-B may be implanted using a standard needle for simple placement, as compared with the complicated placement of DRG leads in the foramen. FIG. 2C illustrates how the branches 212 collapse against the lead body 210 when inserted in a catheter sheath 220. FIG. 2D shows how the branches 212 extend away from the lead body 210 as the sheath 220 is removed. The sheath 220 can slide back over the branches 212 if the lead requires repositioning. The branches 212 may comprise shape memory materials or have a pre-defined shape that is set based on body temperatures or other parameters.

The shape of the lead may also be modified such that the lead is bent to be positioned proximate target structures that are not in vertical alignment along the spinal column. For example, a lead may be pre-bent within a straight stylet such that the shaped curves are activated by one or more of heat, light, or shape memory materials once the stylet is removed upon insertion. The lead may include one or more directional markers as well. The curvature may be used to anchor the lead, for example, around a target location such as a pedicle. The lead may also include an anchor at the tip for placement. The curvature may be predefined to selectively position one or more electrodes proximate a target structure such as one or more nerve roots and/or DRGs. Since the curvature of the lead may be three-dimensional, electrode spacing may be further customized for a patient or therapy. A shaped lead may include any combination of the described curvatures with the branched configurations discussed above.

A curved, or bent, lead provides various options for electrode programming. For example, stimulation parameters may includes combinations of cathode and anodal stimulation at multiple targets at the same time. In certain embodiments, a cathode may be placed over a nerve root and an anode over dorsal columns or a dorsal root entry zone. This can allow for stimulation laterally and over the midline on the same lead, thereby reducing the number of leads needed. The multiple stimulation options on a single lead can also treat multiple types of pain simultaneously (e.g., general dermatomes along the dorsal column to address back pain while also covering a focused nerve root). These leads may be implanted with a transgrade technique. Also, in certain embodiments, the bendable lead may be used to create diagonal stimulation fields since the electrical field may be oriented based on electrode selection and individual control as set forth above. Examples of lead shapes that can achieve these fields are discussed below.

Figure 3A:
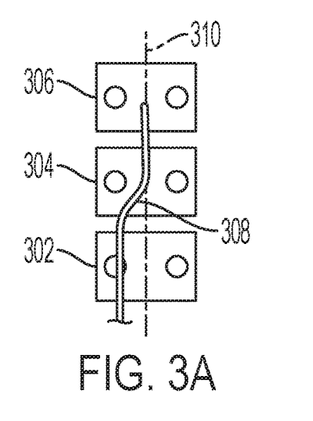
FIGS. 3A-F are front views of bendable leads implanted in the spinal epidural space according to various example embodiments.
Figure 3B:
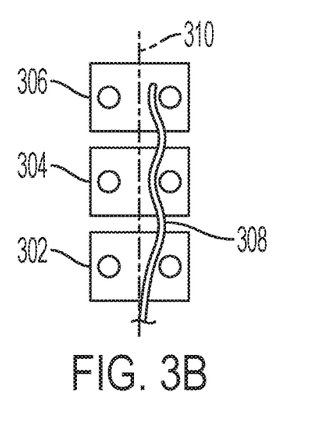
Figure 3C:
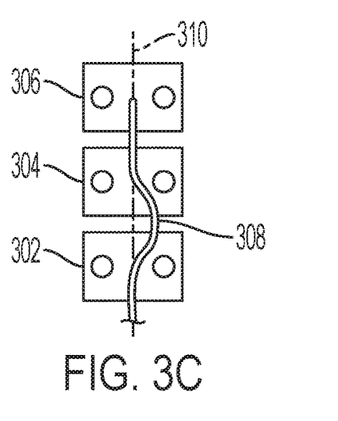
Figure 3D:
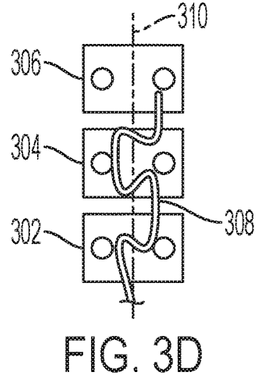
Figure 3E:
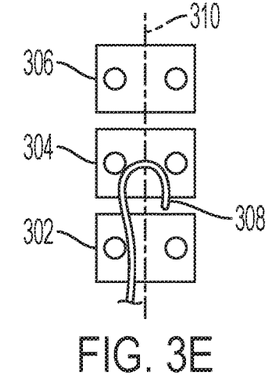
Figure 3F:
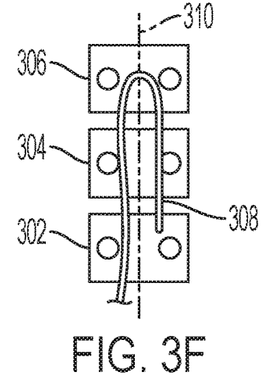

FIGS. 3A-H illustrate example shaped (e.g., bent, curved) leads in accordance with various embodiments. These leads operate electrodes along the midline as well as laterally in the epidural space. In certain embodiments, a curve leaves a midline ECAP recording contact in place. In FIG. 3A, a lead 308 is placed proximate one or more target neural structures (e.g., a nerve root or DRG) along the left side of vertebrae 302, 304 and then curves back to the midline 310 proximate vertebra 306. In FIG. 3B, a lead 308 is placed proximate a plurality of target neural structures along one side of the spinal column (shown as to the right of midline 310). In FIG. 3C, a lead 308 runs along the midline 310 and curves to one side to target a specific neural structure. In the example embodiment of FIG. 3D, a lead 308 is curved to target neural structures on opposing sides of the midline 310 along adjacent vertebrae in a zig-zag pattern. In FIGS. 3E and 3F, a lead 308 curves around back on itself to target neural structure on opposing sides of the midline 310 for a single vertebra (e.g., FIG. 3E) or for multiple vertebrae (e.g., FIG. 3F). These paper clip shaped leads can sense from a lateral position proximate a nerve root or DRG to stimulate at a midline position, or vice versa. The morphology is different depending upon where electrodes sense.

Figure 3G:
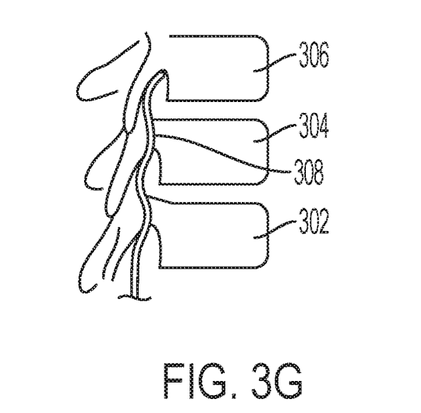
FIGS. 3G-H are side views of bendable leads anchored at a vertebral pedicle according to example embodiments.
Figure 3H:
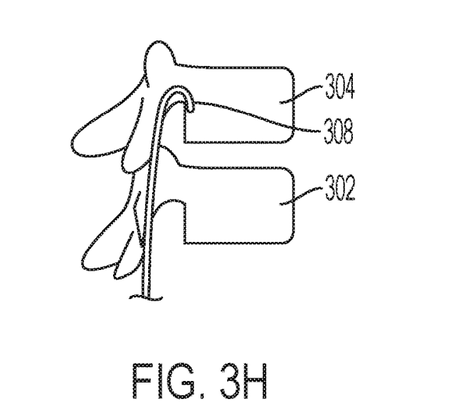

As each of the shaped leads is shaped and positioned to specifically target predefined neural structures, anchoring the lead 308 not only sets the proper placement of electrodes for stimulating target structures, it also mitigates or avoids motor stimulation or stimulation of anterior root fibers, which are uncomfortable. As set forth above, the tip of the lead may be used to anchor the lead within the epidural space, including anchoring at a nerve root by curving down between nerve roots in the epidural space. FIG. 3G illustrates a side view of a lead 308 extending along vertebrae 302, 304, and 306 and curved (e.g., threaded) in the dorsal and ventral directions to target neural structures at each vertebra. FIG. 3H illustrates an example lead 308 that is curved at the end to anchor the lead 308 at a nerve root or other neural structure. With a lead shaped to target specific neural structures, the spacing of electrodes along the lead is also necessary and discussed further below.

Figure 4A:
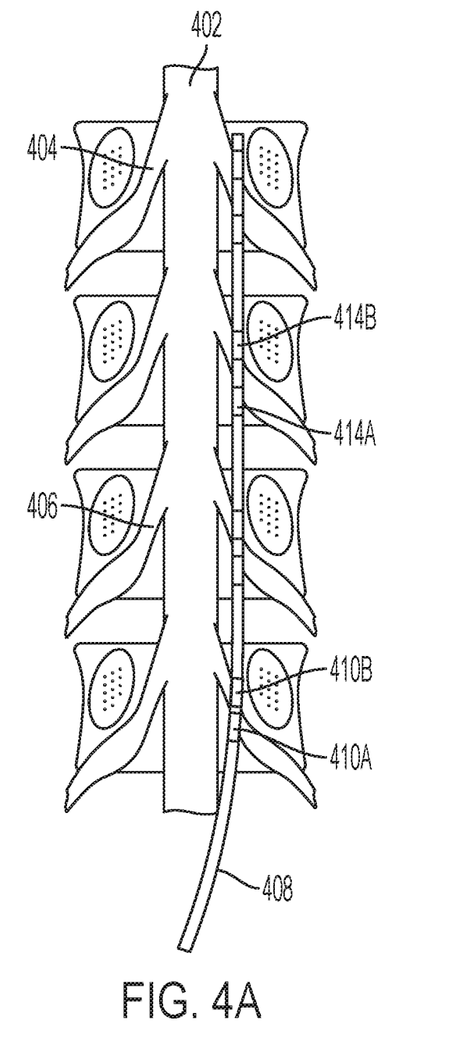
FIG. 4A is a front view of an implanted lead with variable spacing between the two electrodes of the lead pairs according to an example embodiment.
Figure 4B:
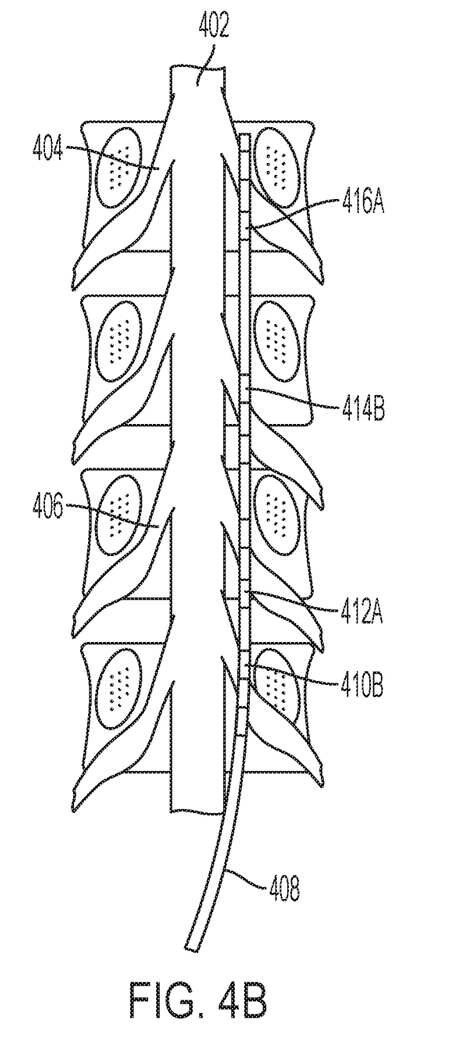
FIG. 4B is a front view of an implanted lead with variable spacing between the lead pairs according to an example embodiment.

FIGS. 4A and 4B illustrate different spacing configurations for electrodes along the shaped leads discussed above. In certain embodiments, the spacing between two electrodes in an electrode pair may be varied as shown in FIG. 4A. A lead 408 is shown extending over four neural structures (here nerve roots 404) of adjacent levels of a patient's spinal column 402. As set forth above, the lead 408 could cover one or more nerve roots 404 and/or DRGs 406. Each nerve root 404 is covered by a pair of electrodes (e.g., 410A, 410B). To improve targeting stimulation at each desired nerve root 404, the spacing within each electrode pair can be varied. For example, electrodes 410A and 410B are spaced a distance D1 apart (measured from the center of electrode 410A to the center of electrode 410B) whereas electrodes 414A and 414B are spaced distance D2 apart and D1 D2. Example distances for D1 and D2 include 3 mm to 14 mm, or, in certain embodiments, a distance of 3 mm. Alternatively, the distances may be configured as a ratio of a distance between electrodes per the length of the lead or per number of electrodes present. An electrode configuration including skipped bipoles over the spinal cord may be effective and have a distance of about 14 mm. The spacing may be determined by the size (e.g., width) of the respective targeted neural structures. The spacing may also be controlled by placement of electrodes of different sizes. Electrodes may have a diameter in a range of sizes such as less than 1 mm to 1.5 mm, or 1 mm to 1.3 mm or even a diameter of 1 mm. The electrode heights may be in a range of 1-8 mm, where certain embodiments involve a height of 4 mm. This is further customized when a single lead is shaped to target a mixture of nerve roots 404 and DRGs 406.

In FIG. 4B, spacing variation between electrode pairs is illustrated. The spacing variations of FIGS. 4A and 4B may be used in any combination. For interelectrode pair spacing, the space between the second electrode of a first pair and a first electrode of a subsequent pair is varied. As shown, the neural target structures of the spinal column 402 are not evenly spaced apart. Therefore, electrodes 410B and 412A are spaced apart by a distance D3, and electrodes 414B and 416A are spaced apart by a distance D4, where D3 D4. Example distances for D3 and D4 include 10 mm to 35 mm depending on the patient and location of the neural structures. There is a lot of variability with respect to a patient's height, degeneration of the intervertebral discs, etc. In addition, in the cervical region the distances would be smaller, closer to 10 mm, and larger in the lumbar region, up to about 35 mm. Alternatively, the distances may be configured as a ratio of a distance between electrode pairs per the length of the lead or per number of electrodes present.

The varying distances between the electrode pairs may be due to varying distances between neural structures (e.g., adjacent nerve roots); due different lengths of cervical, thoracic, and lumbar levels; and/or due to different sized patient heights. The sizing can be measured by fluoroscopy for customization for a patient, for example by measure pedicle spacing. In various embodiments, the spacing may be 3, 3, 2 spacing for an eight-contact lead, which could also anticipate migration by providing redundancy in ⅔ of the pairs. In other leads, two four-contact electrode clusters may protect against migration. As discussed above, the electrodes can be individually controlled, or segments of a directional electrode may be individually controlled, to turn tripolar leads into monopolar leads. As set forth, a lead may also include more than eight contacts, which provides additional spacing options. The electrodes are controlled by a control unit as part of a medical device discussed further below.

Figure 5:
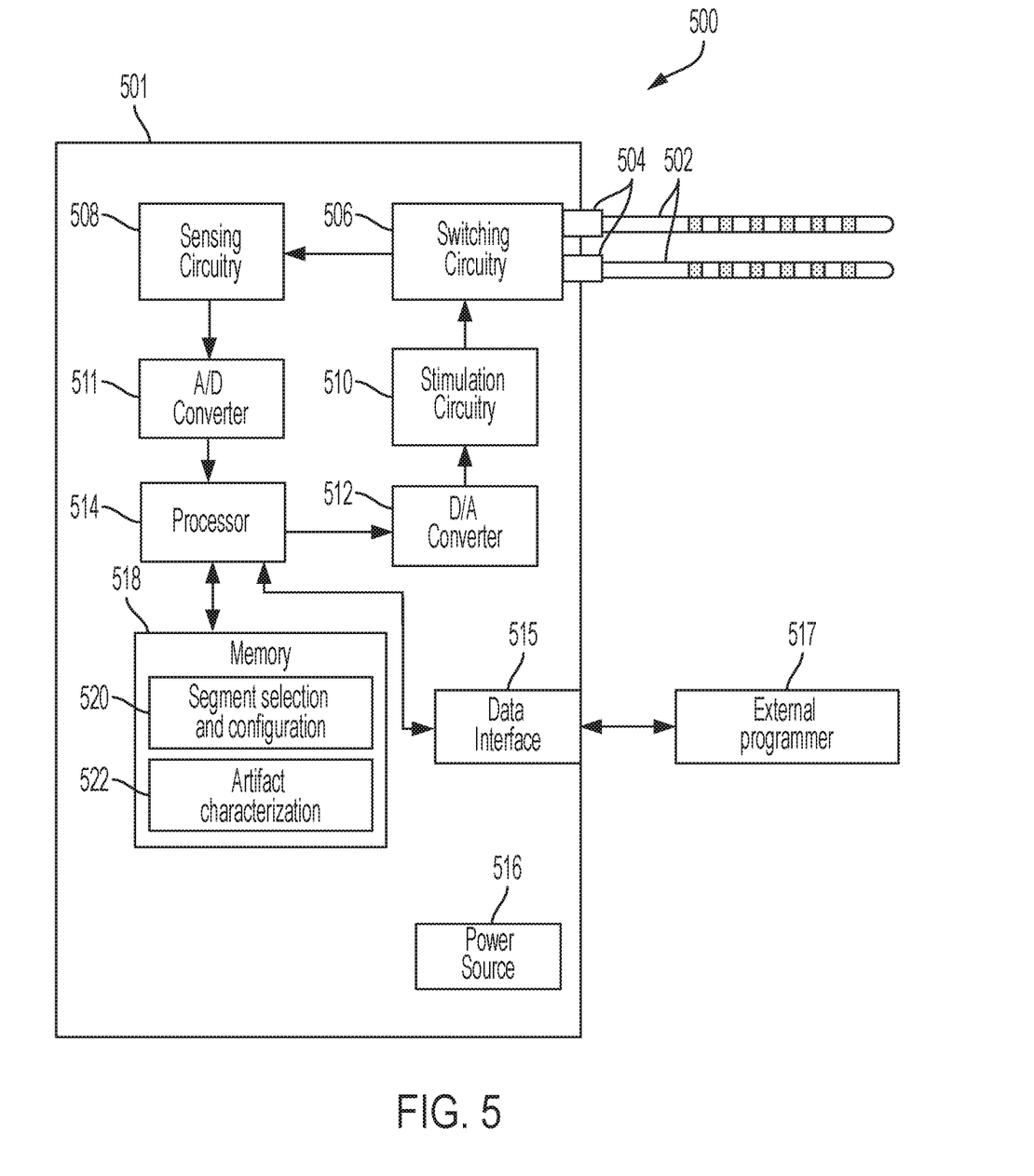
FIG. 5 is a block diagram of an apparatus according to an example embodiment.

In FIG. 5, a block diagram shows an implantable system 500 according to an example embodiment. The system includes a control unit 501 which is a self-contained unit that may be implanted within the patient or located externally. One or more leads 502 are coupled to the control unit 501 via connectors 504. The control unit 501 includes switching circuitry 506 that selectively couples electrodes (and segments thereof, if so equipped) to individual circuit elements within the control unit 501. For example, electrodes may be coupled to sensing circuitry 508 that receives signals generated by electrodes configured as sensing electrodes. Other electrodes (or the same electrodes at different times) may be coupled to stimulation circuitry 510 that delivers electrical signals (e.g., pulse waveforms) that are delivered to target tissue via the electrodes.

The switching, sensing, and stimulation circuitry 508, 510 may include analog processing circuitry such as preamplifiers, amplifiers, filters, etc. As the control unit 501 may use digital signal processing, the unit 501 may utilize an analog-to-digital converter 511 and/or a digital-to-analog converter 512. These facilitate digital signal processing via one or more processors 514. The processor may include any combination of central processing units, co-processors, digital signal processors, application specific integrated circuits, etc. The one or more processors 514 are coupled to memory 518, which may include any combination of volatile memory (e.g., random access memory) and non-volatile memory (e.g., firmware, flash memory).

Each processor 514 operates in response to instructions stored in the memory 518. Those instructions may include a segment selection and configuration function 520 that assists in setup of leads with one or more segmented electrodes. The instruction may also include a stimulation artifact characterization function 522 that enables sensor electrodes with exposed or activated surfaces facing away from the target tissue to accurately characterize stimulation artifacts.

The control unit 501 may be able to be programmed and/or controlled via an external programmer 517. The external programmer 517 links with a data interface 515 of the device. The data interface 515 may facilitate communications via any combination of wireless media, wired media, optical media, etc. The external programmer 517 may send control instructions to the control unit 510, add software/firmware to the unit 510, update software/firmware of the unit 510, and/or download data gathered by the unit 510. The control unit 510 may also include a self-contained power source 516, e.g., battery, capacitors, generator/converter, etc.

As described herein, the selection and spacing of electrodes among electrodes and between electrode pairs on a shaped lead implanted in the epidural space can specifically target neural structures such as nerve roots and DRGs to provide the benefits of nerve root and DRG stimulation without the negative effects of placing a lead in the foramen. The embodiments described herein provide improved patient safety as well as comfort.

ILLUSTRATIVE EMBODIMENTS

The technology described herein is defined in the claims. However, below is provided a non-exhaustive listing of non-limiting embodiments. Any one or more of the features of these embodiments may be combined with any one or more features of another example, embodiment, or aspect described herein.

In illustrative Embodiment 1, a system comprises a bendable, pre-formed lead body operable to be implanted proximate a neural pathway of a patient. A first electrode comprises a plurality of first segments at a first longitudinal location of the lead body and is configured to be positioned at a lateral epidural region proximate at least one nerve root of the patient. A second electrode comprises a plurality of second segments at a second longitudinal location of the lead body and is configured to be positioned along a midline of the patient's spinal column. A signal generator is electrically coupled to at least one of the first and second electrodes, and a processor is coupled to the signal generator and operable to apply a stimulation signal to at least one of the first and second electrodes.

In illustrative Embodiment 2, a system comprises the system of Embodiment 1 wherein at least one of the first segments and the second segments are individually programmable to steer an electric field. In illustrative Embodiment 3, a system comprises the system of Embodiment 2 wherein the field is a diagonal field. In illustrative Embodiment 4, a system comprises the system of any one of the preceding Embodiments wherein the first electrode is coupled to a sensing circuit that senses biopotentials and the second electrode is coupled to the signal generator to apply a stimulation signal.

In illustrative Embodiment 5, a system comprises the system of any one of the preceding Embodiment wherein the lead body comprises a main lead portion and one or more branch portions, where each branch portion is coupled to the lead body at a proximal end and separated from the lead body at a distal end wherein the distal end is movable with respect to the lead body. In illustrative Embodiment 6, a system comprises the system of Embodiment 5, wherein the first electrode is positioned on the main lead portion and the second electrode is positioned on a branch portion.

In illustrative Embodiment 7, a system comprises a lead body operable to be implanted proximate a target nerve root area of a patient. A first electrode is located at a first longitudinal location of the lead body, and a second electrode is located at a second longitudinal location of the lead body forming a pair of electrodes with the first electrode. The second electrode is spaced apart from the first electrode at a distance, D, determined by at least one of the size of the target nerve root area and distance between the electrode pair and the target nerve root area. A signal generator is electrically coupled to at least one of the first and second electrodes, and a processor is coupled to the signal generator and operable to apply a stimulation signal to at least one of the first and second electrodes.

In illustrative Embodiment 8, a system comprises the system of Embodiment 7 wherein the distance between the electrode pair and the target nerve root area determines a depth of field penetration into the target nerve root area. In illustrative Embodiment 9, a system comprises the system of one of Embodiments 7 and 8 wherein D is determined by the orientation of stimulation applied to the target nerve root area. In illustrative Embodiment 10, a system comprises the system of any one of Embodiments 7 through 9 wherein D is about 3 mm from the center of the first electrode to the center of the second electrode.

In illustrative Embodiment 11, a system comprises a system of any one of Embodiments 7 through 10 wherein a size of the first and second electrodes is determined by at least one of the size of the target nerve root area and distance between the electrode pair and the target nerve root area. In illustrative Embodiment 12, a system comprises the system of Embodiment 11 wherein the size of the first and second electrodes is 1 mm in diameter.

In illustrative Embodiment 13, a system comprises the system of any one of Embodiments 7 through 12 further comprising a third electrode located at a third longitudinal location of the lead body proximate a second target nerve root area, and a fourth electrode located at a fourth longitudinal location of the lead body forming a second pair of electrodes with the third electrode and coupled to the signal generator and processor. The fourth electrode is spaced apart from the third electrode at a second distance, different from D, determined by at least one of the size of the second target nerve root area and distance between the second electrode pair and the second target nerve root area.

In illustrative Embodiment 14, a system comprises the system of any one of Embodiments 7 through 13 wherein D is determined based on a measurement of spacing between the patient's pedicles. In illustrative Embodiment 15, a system comprises the system of any one of Embodiments 7 through 14 further comprising a segmented electrode positioned outside the target nerve root area and coupled with the first pair of electrodes. In illustrative Embodiment 16, a system comprises the system of any one of Embodiments 7 through 15 wherein the lead body is a bendable, pre-formed lead body configured to anchor the lead body to a nerve root.

In illustrative Embodiment 17, a system comprises a lead body operable to be implanted proximate a plurality of nerve roots of a patient. A first set of electrodes is located at a first longitudinal location of the lead body, and a second set of electrodes is located at a second longitudinal location of the lead body. The second set of electrodes is spaced apart from the first set of electrodes by a first distance determined by a spacing between a first nerve root and a second nerve root of the patient. A third set of electrodes is located at a third longitudinal location of the lead body and the third set of electrodes is spaced apart from the second set of electrodes by a second distance, wherein the second distance is different from the first distance and determined by a spacing between the second nerve root and a third nerve root of the patient. A signal generator is electrically coupled to at least one of the first and second electrodes, and a processor is coupled to the signal generator and operable to apply a stimulation signal to at least one of the first and second electrodes.

In illustrative Embodiment 18, a system comprises the system of Embodiment 17 wherein at least one of the sets of electrodes includes segmented electrodes having individually programmed segments configured to steer a stimulation field.

In illustrative Embodiment 19, a system comprises the system of one of Embodiments 17 and 18 wherein the lead body is a bendable, pre-formed lead body configured to position the first set of electrodes proximate the first nerve root of the patient, position the second set of electrodes proximate the second nerve root of the patient, and position the third set of electrodes proximate the third nerve root of the patient based on orientation of stimulation applied to the respective nerve roots.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

The foregoing description has been presented for the purposes of illustration and description. It is not intended to be exhaustive or to limit the embodiments to the precise form disclosed. Many modifications and variations are possible in light of the above teachings. Any or all features of the disclosed embodiments can be applied individually or in any combination and are not meant to be limiting, but purely illustrative. It is intended that the scope of the invention be limited not with this detailed description, but rather, determined by the claims appended hereto.

What is claimed is:

1. A system comprising:
a bendable, pre-formed lead body operable to be implanted proximate a neural pathway of a patient;
a first electrode comprising a plurality of first segments at a first longitudinal location of the lead body and configured to be positioned at a lateral epidural region proximate at least one nerve root of the patient;
a second electrode comprising a plurality of second segments at a second longitudinal location of the lead body and configured to be positioned along a midline of the patient's spinal column;
a signal generator electrically coupled to at least one of the first and second electrodes; and
a processor coupled to the signal generator and operable to apply a stimulation signal to at least one of the first and second electrodes,
wherein the first electrode is coupled to the signal generator to apply a stimulation signal and the second electrode is coupled to a sensing circuit that senses biopotentials.

2. The system of claim 1, wherein at least one of the first segments and the second segments are individually programmable to steer an electric field.

3. The system of claim 2, wherein the field is a diagonal field.

4. The system of claim 1, wherein the lead body comprises a main lead portion and one or more branch portions, where each branch portion is coupled to the lead body at a proximal end and separated from the lead body at a distal end wherein the distal end is movable with respect to the lead body.

5. The system of claim 4, wherein the first electrode is positioned on the main lead portion and the second electrode is positioned on a branch portion.

6. The system of claim 1, wherein the sensing circuit is configured to sense evoked compound action potential (ECAP) signals.

7. A system comprising:
a lead body operable to be implanted proximate at least one target nerve root area of a patient;
a first electrode at a first longitudinal location of the lead body;
a second electrode at a second longitudinal location of the lead body forming a first pair of electrodes with the first electrode, the second electrode spaced apart from the first electrode at a distance, D, determined by at least one of the size of a first target nerve root area and distance between the first electrode pair and the first target nerve root area;
a third electrode at a third longitudinal location of the lead body proximate a second target nerve root area;
a fourth electrode at a fourth longitudinal location of the lead body forming a second pair of electrodes with the third electrode, the fourth electrode spaced apart from the third electrode at a second distance, different from D, determined by at least one of the size of the second target nerve root area and distance between the second electrode pair and the second target nerve root area;
a signal generator electrically coupled to at least one of the first and second electrodes and at least one of the third and fourth electrodes; and
a processor coupled to the signal generator and operable to apply a stimulation signal to at least one of the first and second electrodes and at least one of the third and fourth electrodes,
wherein at least a portion of the lead body containing the first longitudinal location, the second longitudinal location, the third longitudinal location, and the fourth longitudinal location is configured to be implanted parallel to a midline of a patient spinal column, and wherein the first electrode pair and the second electrode pair are spaced apart at a third distance determined by the patient spinal column anatomy.

8. The system of claim 7, wherein the distance between the first electrode pair and the first target nerve root area determines a depth of field penetration into the target nerve root area.

9. The system of claim 7, wherein D is determined by the orientation of stimulation applied to the target nerve root area.

10. The system of claim 7, wherein D is about 3 mm from the center of the first electrode to the center of the second electrode.

11. The system of claim 7, wherein a size of the first and second electrodes is determined by at least one of the size of the first target nerve root area and distance between the first electrode pair and the first target nerve root area.

12. The system of claim 11, wherein the size of the first and second electrodes is 1 mm in diameter.

13. The system of claim 7, wherein D is determined based on a measurement of spacing between the patient's pedicles.

14. The system of claim 7, further comprising a segmented electrode positioned outside the first target nerve root area and coupled with the first pair of electrodes.

15. A system comprising:
- a lead body operable to be implanted proximate a plurality of nerve roots of a patient;
- a first set of electrodes at a first longitudinal location of the lead body;
- a second set of electrodes at a second longitudinal location of the lead body, the second set of electrodes spaced apart from the first set of electrodes by a first distance determined by a spacing between a first nerve root and a second nerve root of the patient;
- a third set of electrodes at a third longitudinal location of the lead body, the third set of electrodes spaced apart from the second set of electrodes by a second distance, wherein the second distance is different from the first distance and determined by a spacing between the second nerve root and a third nerve root of the patient;
- a signal generator electrically coupled to at least one of the first and second electrodes; and
- a processor coupled to the signal generator and operable to apply a stimulation signal to at least one of the first and second electrodes,
- wherein at least a portion of the lead body containing the first longitudinal location, the second longitudinal location, and the third longitudinal location is configured to be implanted parallel to a midline of a patient spinal column.

16. The system of claim 15, wherein at least one of the sets of electrodes includes segmented electrodes having individually programmed segments configured to steer a stimulation field.

* * * * *